US006635668B1

(12) United States Patent
Tidwell et al.

(10) Patent No.: US 6,635,668 B1
(45) Date of Patent: Oct. 21, 2003

(54) IMIDAZOLINE RECEPTOR BINDING COMPOUNDS

(75) Inventors: Richard R. Tidwell, Pittsboro, NC (US); James E. Hall, Chapel Hill, NC (US); Dorothy H. Wood, Hillsborough, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 09/120,584

(22) Filed: Jul. 22, 1998

(51) Int. Cl.[7] ................. A61K 31/343; A61K 31/4184; A61K 31/155

(52) U.S. Cl. .............. 514/394; 514/411; 514/461; 514/636; 514/637

(58) Field of Search .................. 514/394, 411, 514/461, 636, 637

(56) References Cited

U.S. PATENT DOCUMENTS

| | | | |
|---|---|---|---|
| 5,428,051 A | 6/1995 | Tidwell et al. | 514/394 |
| 5,574,059 A | 11/1996 | Regunathan et al. | 514/397 |
| 5,602,172 A | 2/1997 | Boykin et al. | 514/461 |
| 5,627,184 A | 5/1997 | Boykin et al. | 514/256 |
| 5,639,755 A | 6/1997 | Dykstra et al. | 514/256 |
| 5,643,935 A | 7/1997 | Dykstra et al. | 514/394 |
| 5,668,167 A | 9/1997 | Tidwell et al. | 514/411 |
| 5,686,477 A | 11/1997 | Jarry et al. | 514/377 |
| 5,723,495 A | 3/1998 | Hall et al. | 514/633 |
| 5,726,197 A | 3/1998 | Clark et al. | 514/387 |

OTHER PUBLICATIONS

Wood et al., European Journal of Pharmacology, vol.. 353(1), pp. 97–103, Jul. 1998.*

D. H. Wood et al.; *Pentamidine is a Potent Inhibitor of Radioligand Binding to Imidazoline Receptors*, Abstracts of Interscience Conf. On Antimicrobial Agents and Chemotherapy 37:280 (1997).

M. Pigini et al.; *Imidazoline Receptors: Qualitative Structure–Activity Relationships and Discovery of Tracizoline and Benazoline. Two Ligands with High Affinity and Unprecedented Selectivity*, Bio. & Med. Chem. 5, No. 5:833–841 (1997).

D. H. Wood et al.; *1, 5–Bis(4–amidinophenoxy)pentane(pentamidine) is a Potent Inhibitor of* [$^3$H]*idazoxan Binding to Imidazoine* $I_2$ *Binding Sites*, Euro. J. of Pharmacology 353:97–103 (1998).

A. Carrieri et al.; *2–D and 3–D Modeling of Imidazoline Receptor Ligands: Insights into Pharmacophore*, Bio. & Med. Chem. 5, No. 5:843–856 (1997).

(List continued on next page.)

Primary Examiner—Edward J. Webman
(74) Attorney, Agent, or Firm—Jenkins, Wilson & Taylor, P.A.

(57) ABSTRACT

Pentamidine and analogs thereof have activity as imidazoline receptor binding compounds. A method of binding the imidazoline receptor, comprises contacting a bis-benzene to said imidazoline receptor in an amount effective to bind to said receptor, wherein said bis-benzene contains at least one amidine group (e.g., one or two). The contacting step may be carried out in vivo or in vitro. Contacting may be carried out with individual active compounds or with libraries of active compounds.

8 Claims, 1 Drawing Sheet

OTHER PUBLICATIONS

D. H. Wood et al.; *Pentamidine is a Potent Inhibitor of [$^3$H]idazoxan Binding to Imidazoine $I_2$ Receptors*, Annals New York Academy of Sciences 110–113 (undated) (XP–000892876).

B. Tao et al.; *Novel Bisbenzamidines and Bisbenzamidazolines as Noncompetitive NMDA Receptor Antagonists*, Bio. & Med. Chem. Ltrs 9:1299–1304 (1999).

A. Yu et al.; *Imidazoline Receptor Agonist Drugs: A New Approach to the Treatment of Systemic Hypertension*, J. Clin. Pharmacol. 36:98–111 (1996).

S. Regunathan et al.; *Imidazoline Receptors and Their Endogenous Ligands*, Annu. Rev. Pharmacol. Toxicol. 36:511–544 (1996).

G. J. Molderings; *Imidazoline Receptors: Basic Knowledge, Recent Advances and Future Prospects for Therapy and Diagnosis*, Drugs of the Future 22(7):757–772 (1997).

C. Farsang et al.; *Imidazoline Receptors: From Discovery to Antihypertensive Therapy (facts and doubts)*, Brain Res. Bulletin 49(5):317–331 (1999).

International Search Report for PCT/US99/14428.

* cited by examiner

IMIDAZOLINE RECEPTOR BINDING COMPOUNDS

FIELD OF THE INVENTION,

The present invention concerns compounds that have high affinity for the imidazoline receptor, particularly the imidazoline I2 receptor, methods of use thereof, and combinatorial libraries thereof.

BACKGROUND OF THE INVENTION

In the early 1980's while studying the different hypotensive effects of imidazoline compounds vs. catecholamines in the nucleus reticularis lateralis, Bousquet et al. proposed the existence of a class of imidazoline (I) binding sites distinct from adrenergic receptors (Bousquet, P. et al., *The Journal of Pharmacology and Experimental Therapeutics* 230:232–236 (1984)).

Many subsequent studies have supported the presence of these binding sites in a variety of tissues (Coupry, I. et al., *Biochemical & Biophysical Research Communications* 147:1055–1060 (1987); Ernsberger, P. R. et al, *European Journal of Pharmacology* 134:1–13 (1987); Meeley, M. P. et al., *Life Sciences*, 38:1119–1126 (1986); Parini, A. et al. *Journal of Biological Chemistry* 264(20): 1874–8 (1989)), including the existence of the putative endogenous ligand (Atlas, D., and Y. Burstein, *European Journal of Biochemistry* 144:287–293 (1984); Li, G. et al., *Science* 263:966–969 (1994)) and purification of a mitochondrial imidazoline binding site (Limon, I. et al., *Journal of Biological Chemistry* 267(30):21645–9 (1992)).

The binding sites are classified into two groups, $I_1$ and $I_2$, according to their affinity for clonidine and idazoxan, respectively, and are located on the plasma and outer mitochondrial membranes. $I_2$ binding sites are associated with the monoamine oxidase protein in certain tissues and are further sub-classified into $I_{2A}$ and $I_{2B}$ depending on their sensitivity to the compound amiloride (Regunathan, S., and D. J. Reis, *Annual Review of Pharmacology & Toxicology* 36:511–44 (1996)). A third subgroup classified as $I_{atypical}$ have been identified in the pancreatic β-cell (Morgan, N. G. et al., *Annals of the New York Academy of Sciences* 763:361–73 (1995); Brown, C. A. et al., *British Journal of Pharmacology* 108:312–317 (1993); Chan, S. L., *Clinical Science* 85(6):671–7 (1993)).

The $I_1$ binding sites are localized on the plasma membrane and have been found in the brainstem, kidneys, adrenal chromaffin cells, rat PC12 cells and platelets. Imidazoline $I_1$ receptor agonists which stimulate $I_1$ receptors in the medulla offer a new therapeutic approach to the treatment of hypertension and associated metabolic syndrome comprising of hyperglycemia, hyperinsulinemia, hypertriglyceridemia and low concentrations of high-density lipoprotein cholesterol (Krentz, A. J., and A. J. Evans, *The Lancet* 351:152–153 (1998)). Selectivity for this receptor reduces the adverse effects attributed to stimulation of $\alpha_2$-adrenoceptors such as sedation and dry mouth. Platelet $I_1$ receptors are upregulated in patients suffering with depression and can be downregulated with antidepressant therapy.

$I_2$ binding sites are more widely distributed than $I_1$ sites. They have been found in the nervous system (cerebral cortex, astrocytes, carotid bodies), specific organs (kidneys, liver, pancreas, colon, urethra, placenta), glands (adrenal medulla, prostate) and certain cell types (platelets, adipocytes, vascular cells). Expression of $I_2$ binding sites is upregulated in human brains during aging, and in patients with Alzheimer's disease. Expression is modified in the brains of depressed suicide victims (Regunathan, S., and D. J. Reis, *Annual Review of Pharmacology & Toxicology* 36:511–44 (1996)).

Efforts have been made to identify compounds with imidazoline receptor binding affinity:

U.S. Pat. No. 5,726,197 to Clark et al. describe isoindolinyl derivatives that have imidazoline receptor binding affinity.

U.S. Pat. No. 5,686,477 to Jarry et al. describes various 5-(aryloxymethyl)oxazolines having imidazoline binding activity.

U.S. Pat. No. 5,354,769 to Garcia Sevilla et al. describes benzofuranyl imidazole derivatives having imidazoline receptor binding activity, and various uses thereof.

U.S. Pat. No. 5,732,717 to Watanabe et al. describes the use of 4-chloro-5-(imidazoline-2-ylamino)-6-methoxy-2-methylpyrimidine for treating substance abuse withdrawal.

U.S. Pat. No. 5,574,059 to Regunathan et al. describes the treatment of vascular smooth muscle cell proliferation with certain imidazoline receptor agonists.

Nevertheless, there are relatively few compounds with imidazoline receptor binding affinity available, and there is continued interest in identifying additional imidazoline receptor binding compounds.

SUMMARY OF THE INVENTION

A first aspect of the present invention is a method of binding the imidazoline receptor, comprising contacting a bis-benzene to said imidazoline receptor in an amount effective to bind to said receptor, wherein said bis-benzene contains at least one amidine group. The amidine group is covalently bound to one of the benzene rings, or an amidine group is covalently bound to both of the benzene rings (such compounds and their pharmaceutically acceptable salts are referred to as "active agents" herein). The contacting step may be carried out in vitro (e.g., with cells that express the imidazoline receptor, or with a cell-free preparation comprising the imidazoline receptor) or in vivo (e.g., by administering said compound to a subject afflicted with a disease state which is alleviable by treatment with a compound having high selectivity and affinity for the imidazoline receptor site).

A second aspect of the present invention is a method of identifying imidazoline receptor binding agents, comprising the steps of providing a library of bis-benzene compounds, said bis-benzene compound containing at least one amidine group as described above; and screening said library for compounds that bind to said imidazoline receptor. The library may be a combinatorial library, and the bis-benzene compounds may be immobilized on a solid support in accordance with known techniques (e.g., where only one of the benzene groups has an amidine group covalently bound thereto, the other benzene group may be affixed, e.g., by covalent bond, to the solid support).

The present invention is explained in greater detail in the drawings and specification set forth below.

DETAILED DESCRIPTION OF THE INVENTION

Figure 1:
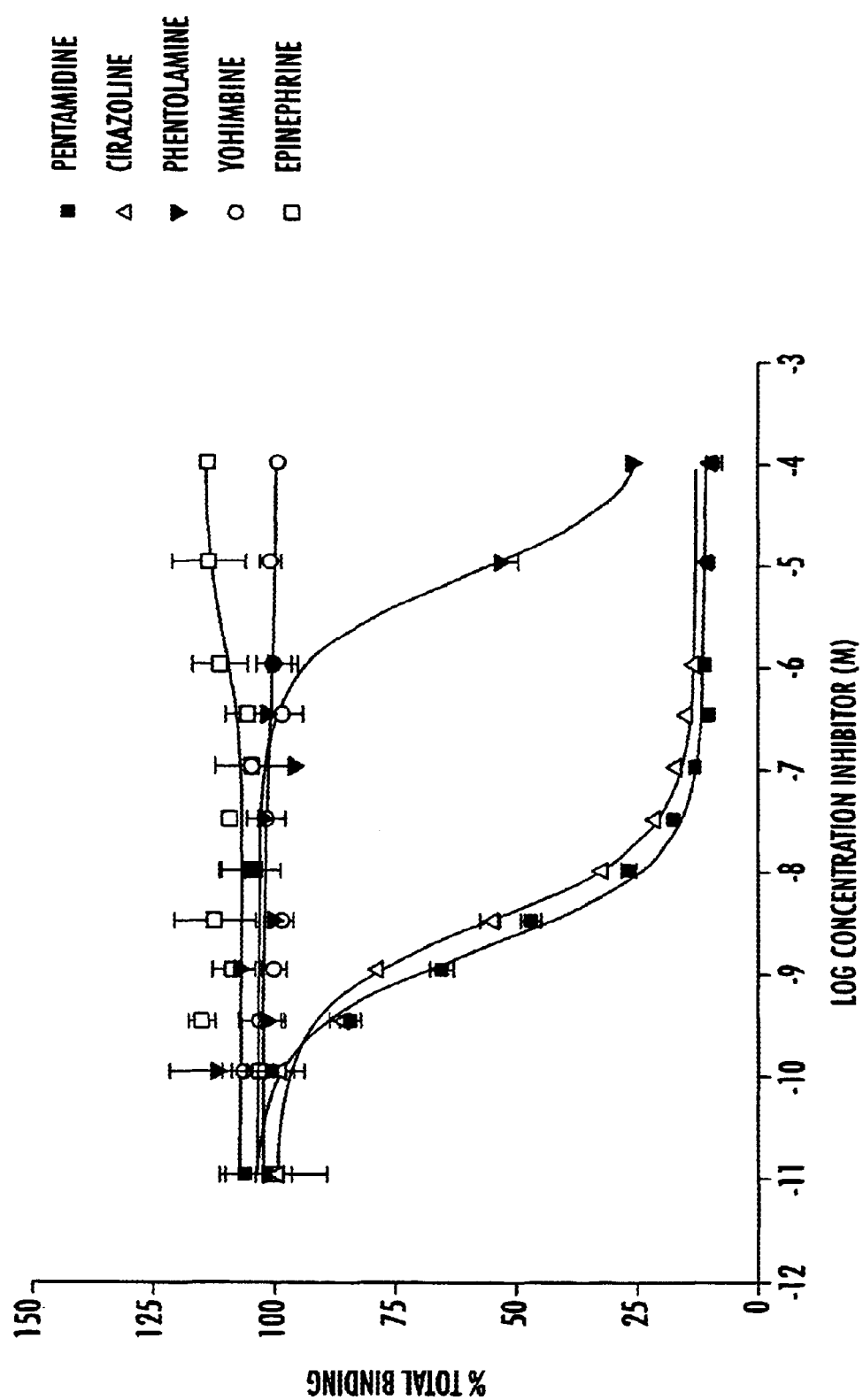
FIG. 1. Inhibition of 5 nM [$^3$H]idazoxan ($K_d$ 14±2 nM) binding to rat liver membranes by $\alpha_2$-adrenoceptor ligands and pentamidine. Cirazoline, $K_i$=3.0±0.4 nM; Phentolamine, $K_i$>5000 nM; Epinephrine, $K_i$>25,000 nM; Yohimbine, $K_i$>25,000 nM; Pentamidine, $K_i$=1.4±0.22 Nm.

Definitions. As used herein:

The term "loweralkyl," as used herein, refers to $C_1$–$C_6$ linear or branched alkyl, such as methyl, ethyl, propyl, isopropyl, butyl, sec-butyl, iso-butyl, tert-butyl, pentyl, isopentyl, and hexyl. Isoalkyl groups, such as isopropyl, isobutyl, isopentyl, and the like are currently preferred. The term "loweralkoxy" or "oxyalkyl" as used herein, refers to $C_1$–$C_6$ linear or branched alkoxy, such as methoxy, ethoxy, propyloxy, butyloxy, isopropyloxy, and t-butyloxy. Methoxy is currently preferred.

"Cycloalkyl" means a saturated monovalent monocyclic hydrocarbon radical containing 3–8 carbon atoms, such as cyclopropyl, cyclobutyl, cyclopentyl, cyclohexyl, cycloheptyl and cyclooctyl.

The term "halo" or "halogen" as used herein refers halogens such as to Cl, Br, I, F, preferably Cl or Br.

"Imidazoline receptor" as used herein refers to any imidazoline receptor, including $I_1$ and $I_2$ receptors. The I2 receptors (including $I_{2A}$ and $I_{2B}$ receptors) are currently preferred. The imidazoline receptor may be of any species of origin, but is preferably mammalian (e.g., human, mouse, rat, cat, dog, rabbit, hamster, monkey, etc.).

"Phenyl" as used herein encompasses all possible isomeric phenyl radicals optionally monosubstituted or disubstituted with a substituent selected from the group consisting of lower alkyl, lower alkoxy, and halo.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"[$^3$H]-idazoxan" refers to tritiated idazoxan, named as (1,4-[6,7-$^3$H]-benzodioxan-2-yl)-2-imidazoline hydrochloride, or [$^3$H]-RX 781094. It is available from Amersham plc.

The term "treatment" as used herein covers any treatment of a disease in a mammal, particularly a human, and includes: (i) preventing the disease from occurring in a subject which may be predisposed to the disease but has not yet been diagnosed as having it; (ii) inhibiting the disease, i.e., arresting its development; or (iii) relieving the disease, i.e., causing regression of the disease.

The term "disease state which is alleviable by treatment with a compound having high selectivity and/or affinity for the imidazoline receptor site" as used herein is intended to cover all disease states which are generally acknowledged in the art to be usefully treated with compounds having high selectivity and affinity for the imidazoline site in general, as described in U.S. Pat. No. 5,726,197 to Clark (see column 4, lines 1–19 therein). Such disease states include, but are not limited to, cerebral ischemia, hypertension, excessive intraocular pressure, parkinsonian disorders, eating disorders, seasonal affective disorders, panic disorders, urinary incontinence, diuresis, fertility disorders (including the treatment of infertiliby by, for example, in vitro fertilization, and use in antifertility), sexual dysfunction, impotence, postnatal depression, mild stress-induced amenorrhoea, and galactonrrhoea, by administering to a mammal in need thereof therapeutically effective amount of a compound as described herein, or a pharmaceutically acceptable salt thereof. In addition, such disease states include depression, Alzheimer's disease and diabetes.

Active compounds. Active compounds of the present invention are, in general, pentamidine and analogs thereof. Numerous such compounds are known. In the present invention both benzene rings need not be substituted with an amidine group: only a single ring need be substituted with an amidine group (though optionally both rings may be substituted with an amidine group). Such compounds are known or can be synthesized in accordance with known techniques (See, e.g., U.S. Pat. Nos. 5,723,495; 5,723,288; 5,686,456; 5,668,167; 5,667,975; 5,643,935; 5,639,755; 5,627,184; 5,622,955; 5,606,058; 5,602,172; 5,594,138; 5,578,631; 5,521,189; 5,428,051; 5,206,236; 5,202,320; 4,963,589; 4,940,723; 4,933,347; 4,619,942; 4,397,863; and 4,324,794 (applicants intend that the disclosures of the compounds disclosed in these references are incorporated by reference herein in their entirety; all of these compounds may be provided with a single amidine group as opposed to two amidine groups). Specific examples of such compounds are set forth below.

A first group of active agents useful for carrying out the present invention are bis-benzenes having the formula I:

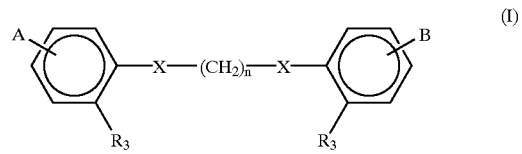

wherein:

A and B are each independently selected from the group consisting of H, loweralkyl, oxyalkyl, nitro, amino, aminoalkyl, halo, hydroxy, carboxy, and compounds of formula (i):

subject to the proviso that at least one of A and B is a compound of formula (i);

$R_1$ and $R_2$ are each independently selected from the group consisting of H, loweralkyl, oxyalkyl, alkoxyalkyl, cyloalkyl, aryl, hydroxyalkyl, aminoalkyl and alkylaminoalkyl; or two $R_1$ group on the same amidine group together represent —($CH_2$)m— wherein m is 2, 3, or 4;

$R_3$ is H, loweralkyl, oxyalkyl, alkoxyalkyl, hydroxyalkyl, cycloalkyl, aryl, aminoalkyl, alkylaminoalkyl or halogen;

n is from 2 to 6; and

X is O, NH, or S;

or a pharmaceutically acceptable salt thereof. In one embodiment, $R_1$, $R_2$ and $R_3$ are H; X is O; and n is 5.

A second group of bis-benzenes that may be used to carry out the present invention are those having formula II:

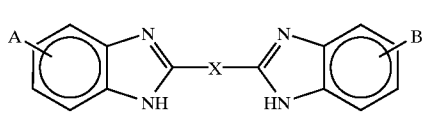

(II)

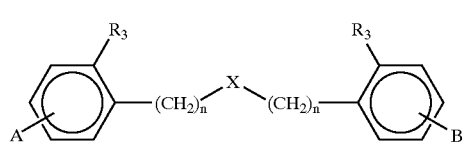

(III)

wherein:

A and B are each independently selected from the group consisting of H, loweralkyl, oxyalkyl, nitro, amino, aminoalkyl, halo, hydroxy, carboxy, and compounds of formula (i):

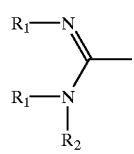

(i)

subject to the proviso that at least one of A and B is a compound of formula (i);

$R_1$ and $R_2$ are each independently selected from the group consisting of H, loweralkyl, oxyalkyl, alkoxyalkyl, cyloalkyl, aryl, hydroxyalkyl, aminoalkyl and alkylaminoalkyl; or two $R_1$ group on the same amidine group together represent —$(CH_2)_m$— wherein m is 2, 3, or 4;

$R_3$ is H, loweralkyl, oxyalkyl, alkoxyalkyl, hydroxyalkyl, cycloalkyl, aryl, aminoalkyl, alkylaminoalkyl or halogen;

X is linear or branched, saturated or unsaturated C1–C12 alkyl containing up to 4 double bonds; or X is a heterocyclic aromatic group selected from the group consisting of:

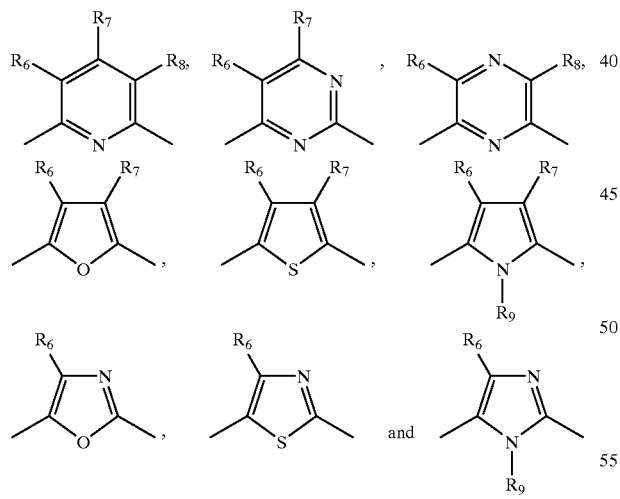

wherein $R_6$, $R_7$, and $R_8$ are each independently selected from the group consisting of H, loweralkyl, halogen, oxyalkyl, oxyaryl, or oxyarylalkyl;

$R_9$ is hydrogen, loweralkyl, hydroxy, aminoalkyl or alkylaminoalkyl;

or the pharmaceutically acceptable salts thereof.

A third group of compounds useful for carrying out the present invention are those having formula III:

wherein:

A and B are each independently selected from the group consisting of H, loweralkyl, oxyalkyl, nitro, amino, aminoalkyl, halo, hydroxy, carboxy, and substituents of formula (i):

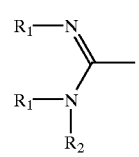

(i)

subject to the proviso that at least one of A and B is a substituent of formula (i);

$R_1$ and $R_2$ are each independently selected from the group consisting of H, loweralkyl, oxyalkyl, alkoxyalkyl, cyloalkyl, aryl, hydroxyalkyl, aminoalkyl and alkylaminoalkyl; or two $R_1$ groups on the same amidine group together represent —$(CH_2)$ m— wherein m is 2, 3, or 4;

$R_3$ is H, loweralkyl, oxyalkyl, alkoxyalkyl, hydroxyalkyl, cycloalkyl, aryl, aminoalkyl, alkylaminoalkyl or halogen;

or two $R_1$ groups on the same amidine group together represent

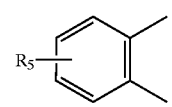

wherein $R_5$ is

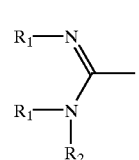

(i)

n is an integer from 0 to 2; and

A is a heterocyclic aromatic group selected from the group consisting of:

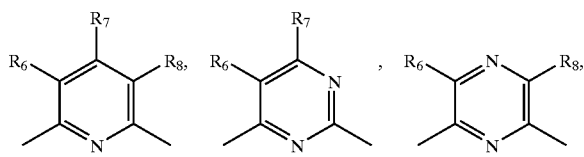

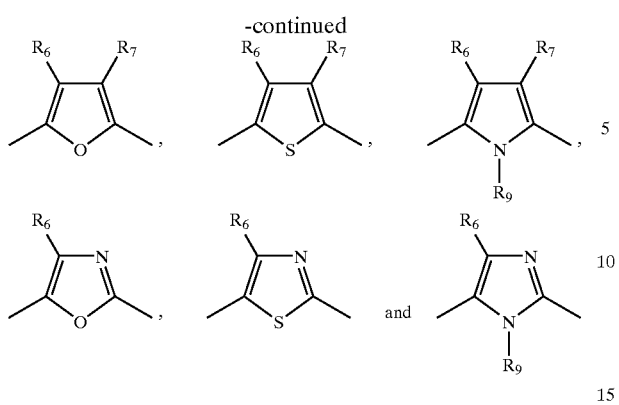

wherein
R$_6$, R$_7$, and R$_8$ are each independently selected from the group consisting of H, loweralkyl, halogen, oxyalkyl, oxyaryl, or oxyarylalkyl;
R$_9$ is hydrogen, loweralkyl, hydroxy, aminoalkyl or alkylaminoalkyl;
and the pharmaceutically acceptable salts thereof.

A fourth group of compounds useful for carrying out the present invention are those having formula IV:

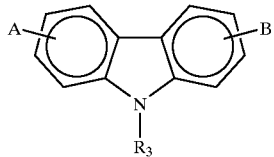

(IV)

wherein:
A and B are each independently selected from the group consisting of H, loweralkyl, oxyalkyl, nitro, amino, aminoalkyl, halo, hydroxy, carboxy, and substituents of formula (i):

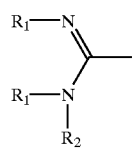

(i)

subject to the proviso that at least one of A and B is a substituent of formula (i);
R$_1$ and R$_2$ are each independently selected from the group consisting of H, loweralkyl, oxyalkyl, alkoxyalkyl, cyloalkyl, aryl, hydroxyalkyl, aminoalkyl and alkylaminoalkyl; or two R$_1$ group on the same amidine group together represent —(CH$_2$)m— wherein m is 2, 3, or 4;
R$_3$ is H, loweralkyl, oxyalkyl, alkoxyalkyl, hydroxyalkyl, cycloalkyl, aryl, aminoalkyl, alkylaminoalkyl or halogen;
or two R$_1$ groups on the same amidine group together represent

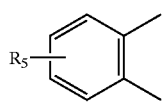

wherein R$_5$ is

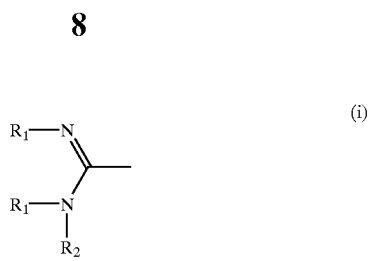

(i)

and the pharmaceutically acceptable salts thereof.

A fifth group of active compounds that may be used to carry out the present invention are those having formula (V):

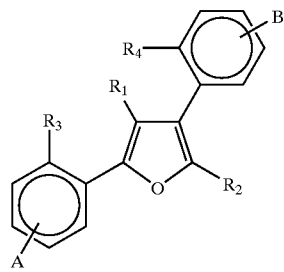

(V)

wherein:

A and B are each independently selected from the group consisting of H, loweralkyl, oxyalkyl, nitro, amino, aminoalkyl, halo, hydroxy, carboxy, and substituents of formula (ii):

(ii)

subject to the proviso that at least one of A and B is a substituent of formula (ii);
R$_1$ and R$_2$ are each independently selected from the group consisting of H, loweralkyl, aryl, alkylaryl, aminoalkyl, aminoaryl, halogen, oxyalkyl, oxyaryl, or oxyarylalkyl;
R$_3$ and R$_4$ are each independently selected from the group consisting of H, loweralkyl, oxyalkyl, alkylaryl, aryl, oxyaryl, aminoalkyl, aminoaryl, or halogen; and
each R$_5$ is independently selected from the group consisting of H, loweralkyl, alkoxyalkyl, hydroxyalkyl, aminoalkyl, alkylaminoalkyl, cycloalkyl, aryl, or alkylaryl or two R$_5$ groups together represent C$_2$ to C$_{10}$ alkyl, hydroxyalkyl, or alkylene; and
R$_6$ is H, hydroxy, loweralkyl, alkoxyalkyl, hydroxyalkyl, aminoalkyl, alkylamino, alkylaminoalkyl, cycloalkyl, hydroxycycloalkyl, alkoxycycloalkyl, aryl, or alkylaryl;

or a pharmaceutically acceptable salt thereof.

A sixth group of active compounds of the present invention are those having formula VI:

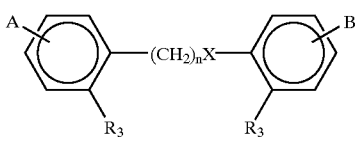

wherein:
A and B are each independently selected from the group consisting of H, loweralkyl, oxyalkyl, nitro, amino, aminoalkyl, halo, hydroxy, carboxy, and substituents of formula (i):

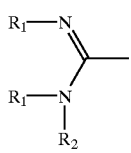

subject to the proviso that at least one of A and B is a substituent of formula (i);
$R_1$ and $R_2$ are each independently selected from the group consisting of H, loweralkyl, oxyalkyl, alkoxyalkyl, cyloalkyl, aryl, hydroxyalkyl, aminoalkyl and alkylaminoalkyl; or two $R_1$ group on the same amidine group together represent —$(CH_2)_m$— wherein m is 2, 3, or 4;
$R_3$ is H, loweralkyl, oxyalkyl, alkoxyalkyl, hydroxyalkyl, cycloalkyl, aryl, aminoalkyl, alkylaminoalkyl or halogen;
or two $R_1$ groups on the same amidine group together represent

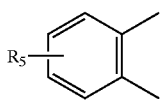

wherein $R_5$ is

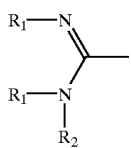

X is O, S or NH;
n is an integer from 1 to 8;
and the pharmaceutically acceptable salts thereof.

Salts of Active Compounds. The active compounds may be converted to a corresponding acid addition salt, or pharmaceutically acceptable salt, by virtue of the presence of the nitrogen atoms.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained at 0°–50° C. The resulting salt precipitates spontaneously or may be brought out of solution with a less polar solvent.

The acid addition salts of the active compounds may be converted to the corresponding free bases by treatment with at least a stoichiometric amount of a suitable base such as sodium or potassium hydroxide, potassium carbonate, sodium bicarbonate, ammonia, and the like.

Utility and Testing. The compounds are generally useful as described above. The compounds may be specifically tested in accordance with known techniques.

In one particular aspect, the invention relates to a method of determining the presence of imidazoline receptors in vitro or in vivo in mammalian tissue, especially human tissue, by contacting the sample suspected of containing such receptors with an active compound of the invention and detecting the presence or absence of binding of such compound to a receptor in the sample. The detecting may be carried out by any suitable means, such as by labelling the active compound with a detectable group such as $^3H$, or by competitive displacement of another receptor binding compound that it itself labelled, all in accordance with known techniques. Detecting may be carried out with a library or combinatorial library of compounds of the invention, as described below.

In another particular aspect, the invention provides methods of alleviating disease states as described above.

Potential for high selectivity and high affinity for imidazoline sites is determined in vitro by a modification of the method of Brown et al., Br. J. Pharmacology, Vol. 99, pp 481 varies as 486 (1990), as described in Example 11 of U.S. Pat. No. 5,726,197 to Clark et al.

Lowering of intraocular pressure is shown in vivo by the method of Moses, R. A., Tr. Am. Acad. Opth. and Otol., January–February 1962: 88–95.

Potential for treatment of cerebral ischemia is shown in vitro by a modification of the method of Gotti et al., Brain Res., Vol 522(2), pp 290–307 (1990).

The antihypertensive activity of the compounds may be determined in conscious spontaneous hypertensive rats prepared with indwelling arterial catheter by the in vivo assay described in Popovic V. and Popovic P., J. Applied. Physiol., Vol. 15, pp. 727–728 (1960), or a modification thereof.

Administration. In applying the compounds of this invention to treatment of the above conditions, administration of the active compounds and salts described herein can be via any of the accepted modes of administration, including oral, parenteral and otherwise systemic route of administration. Any pharmaceutically acceptable mode of administration can be used, including solid, semi-solid or liquid dosage forms, such as, for example, tablets, suppositories, pills, capsules, powders, liquids, suspensions, or the like, preferably in unit dosage forms suitable for single administration of precise dosages, or in sustained or controlled release dosage forms for the prolonged administration of the compound at a predetermined rate. The compositions will typically include a conventional pharmaceutical carrier or excipient and an active compound or the pharmaceutically acceptable salts thereof and, in addition, may include other medicinal agents, pharmaceutical agents, carriers, adjuvants, etc.

The amount of active compound administered will of course, be dependent on the subject being treated, the severity of the affliction, the manner of administration and the judgment of the prescribing physician. However, an effective dose for oral, parenteral and otherwise systemic routes of administration is in the range of 0.01–20 mg/kg/day, preferably 0.1–10 mg/kg/day. For an average 70 kg human, this would amount to 0.7–1400 mg per day, or preferably 7–700 mg/day.

For solid compositions, conventional non-toxic solid carriers include, for example, pharmaceutical grades of mannitol, lactose, cellulose, cellulose derivatives, sodium crosscarmellose, starch, magnesium stearate, sodium saccharin, talcum, glucose, sucrose, magnesium carbonate, and the like may be used. The active compound as defined above may be formulated as suppositories using, for example, polyalkylene glycols, acetylated triglycerides and the like, as the carrier. Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound(s) in an amount effective to alleviate the symptoms of the subject being treated.

Dosage forms or compositions containing active compounds or their salts) in the range of 0.25 to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, cellulose, cellulose derivatives, sodium crosscarmellose, starch, magnesium stearate, sodium saccharin, talcum, glucose, sucrose, magnesium, carbonate, and the like. Such compositions take the form of solutions, suspensions, tablets, pills, capsules, powders, sustained release formulations and the like. Such compositions may contain 1%–95% active ingredient, more preferably 2–50%, most preferably 5–8%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, triethanolamine sodium acetate, etc.

A more recently devised approach for parenteral administration employs the implantation of a slow-release or sustained-release system, such that a constant level of dosage is maintained. See, e.g., U.S. Pat. No. 3,710,795.

The percentage of active compound contained in such parental compositions is highly dependent on the specific nature thereof, as well as the activity of the compound and the needs of the subject. However, percentages of active ingredient of 0.1% to 10% in solution are employable, and will be higher if the composition is a solid which will be subsequently diluted to the above percentages. Preferably the composition will comprise 0.2–2% of the active agent in solution.

In applying the compounds of the invention to treatment of diseases or disorders of the eye which are associated with an abnormally high intraocular pressure, administration may be achieved by any pharmaceutically acceptable mode of administration which provides adequate local concentrations to provide the desired response. These include direct administration to the eye via drops and controlled release inserts or implants, as well as systemic administration as previously described.

Drops and solutions applied directly to the eye are typically sterilized aqueous solutions containing 0.1% to 10%, most preferably 0.5% to 1% of the active ingredient, along with suitable buffer, stabilizer, and preservative. The total concentration of solutes should be such that, if possible, the resulting solution is isotonic with the lacrimal fluid (though this is not absolutely necessary) and has an equivalent pH in the range of pH 6–8. Typical preservatives are phenyl mercuric acetate, thimerosal, chlorobutanol, and benzalkonium chloride. Typical buffer systems and salts are based on, for example, citrate, borate or phosphate; suitable stabilizers include glycerin and polysorbate 80. The aqueous solutions are formulated simply by dissolving the solutes in a suitable quantity of water, adjusting the pH to about 6.8–8.0, making a final volume adjustment with additional water, and sterilizing the preparation using methods known to those in the art.

The dosage level of the resulting composition will, of course, depend on the concentration of the drops, the condition of the subject and the individual magnitude of responses to treatment. However, a typical ocular composition could be administered at the rate of about 2–10 drops per day per eye of a 0.5% solution of active ingredient.

The compositions of the present invention may also be formulated for administration in any convenient way by analogy with other topical compositions adapted for use in mammals. These compositions may be presented for use in any conventional manner with the aid of any of a wide variety of pharmaceutical carriers or vehicles. For such topical administration, a pharmaceutically acceptable non-toxic formulation can take the form of semisolid, liquid, or solid, such as, for example, gels, creams, lotions, solutions, suspensions, ointments, powders, or the like. As an example, the active components may be formulated into a gel using ethanol, propylene glycol, propylene carbonate, polyethylene glycols, diisopropyl adipate, glycerol, water, etc., with appropriate gelling agents, such as Carbomers, Klucels, etc. If desired, the formulation may also contain minor amounts of non-toxic auxiliary substances such as preservatives, antioxidants, pH buffering agents, surface active agents, and the like. Actual methods of preparing such dosage forms are known, or will be apparent, to those skilled in the art; for example, see, e.g., Remington's Pharmaceutical Sciences, Mack Publishing Company, Easton, Pa., 16th Edition, 1980.

Combinatorial chemistry. Numerous methods of synthesizing combinatorial libraries and (where desired) applying such molecules on solid supports (where the molecules may be either covalently or non-covalently bound, linked or attached to the solid support) are known, and such libraries can be made and used in accordance with procedures known to those skilled in the art. See, e.g., J. Baldwin and I. Henderson, *Recent Advances in the Generation of Small-Molecule Combinatorial Libraries: Encoded Split Synthesis* and *Solid-Phase Synthetic Methodology*, Med. Res. Reviews 16, 391–405 (1996); see also U.S. Pat. No. 5,565,324 to Still et al., U.S. Pat. No. 5,284,514 to Ellman et al., U.S. Pat. No. 5,445,934 to Fodor et al. (the disclosures of all United States patents cited herein are to be incorporated herein by reference in their entirety). Libraries of active compounds as described herein (i.e., a group of compounds that have the general definition of active compounds as described herein, but differ from one another in specific structural features, patterns of substitution(s), etc.), may be screened in accordance with known techniques to identify imidazoline receptor binding compounds with specific desired characteristics.

The present invention is explained in greater detail in the following non-limiting examples.

EXAMPLE 1

1. Materials and Methods

Membrane preparation. Membranes were prepared in accordance with known techniques (R. Zonnenchein et al., Eur. J. Pharmacol. 190, 203–215 (1990)). Briefly, male Sprague-Dawley rats (Hilltop, Scottsdale, Pa., USA) weighing approximately 250–300 g were decapitated, their livers rapidly removed and immediately placed into 0.25 M cold sucrose solution. The livers were weighed and minced with scissors before being homogenized at 4° C. in solution A (0.25 M sucrose containing 0.1 mM phenylmethyl sulfonyl fluoride 1:10 v/v) for 1 min using a Biospec homogenizer (Bartlesville, Okla., USA). The homogenate was centrifuged at 600×g for 10 min at 4° C. The resulting pellet was washed with solution A, discarded and the supernatant fractions were combined and centrifuged at 12,000×g for 30 min. This pellet was washed then resuspended in cold buffer B (50 mM Tris/HCl pH 7.4). Using a Bio-Rad (Hercules, Calif., USA) assay kit, the protein concentration was determined using bovine serum albumin as the standard according to the assay of Bradford et al. (Bradford, M. M., 1976. Anal. Biochem. 72, 248–254.). The preparation was stored at −80° C. at a concentration of 20 mg protein/ml.

Saturation binding studies. Binding studies were performed in triplicate in 1 ml buffer B containing [$^3$H]idazoxan (0.1–50 nM). The addition of rat liver membranes at a final concentration of 500 µg protein/ml initiated binding, and the samples were incubated to equilibrium at 22° C. for 45 min. Non-specific binding was defined as the amount of [$^3$H] idazoxan bound in the presence of 10 µM cirazoline.

Competition binding studies. Competition experiments were performed in 1 ml buffer B containing 5 nM [$^3$H] idazoxan. Increasing concentrations of compound were added (1 nM–10 mM) and binding was initiated by the addition of rat liver membranes at a final concentration of 500 µg protein/ml. In all experiments, bound and free radioligand were separated by vacuum filtration through Whatman GF/C filters and washed with 2×10 ml cold buffer B. Radioactivity on filters was determined by liquid scintillation spectroscopy using a Packard Tri-Carb 2100TR. Samples were run in triplicate and the results were derived from at least three experiments with the exception of Compounds 4 and 8 which were run twice due to limited quantities.

Anti-Pneumocystis carinii activity. Induction, treatment and evaluation of *P. carinii* pneumonia in the rat was carried out according to methods described previously (Jones, S. K. et al., Antimicrob. Agents Chemother. 34, 1026–1030 (1990)). To summarize the scoring procedure, the mean histologic scores were determined by two examiners using a blinded protocol. *P. carinii* cysts were counted in the stained lung sections and assigned the following values; 0.5—less than 10 cysts counted per two fully examined sections; 1—scattered cysts with less than 10% of the lung tissue involved; 2—scattered cysts with limited intense focal involvement and 10 to 25% of lung tissue involved; 3—scattered cysts with numerous intense areas of focal involvement and 26 to 50% of lung tissue involved; 4—cysts found throughout the tissue with numerous intense focal areas of involvement having greater than 50% of lung tissue involved.

Chemical synthesis. The procedure for the synthesis of 4-methoxybenzamidine was adapted from Tidwell et al. (J. Med. Chem. 33, 1252–1257 (1990)). The procedure was altered in the following way; a solution of 1,4-dioxane was cooled to −10° C. and presaturated with hydrogen chloride (HCl) gas. 4-Methoxybenzonitrile and anhydrous ethanol were added and the reaction mixture was saturated with HCl gas. The reaction flask was sealed and stirred at ambient temperature for twelve days. The imidate was collected and dried under high vacuum for 20 min and then dissolved in ethanolic ammonia at −10° C. The reaction mixture was stirred at room temperature overnight. The purification of 4-methoxybenzamidine was followed according to the published procedure. All other compounds were synthesized as previously described (B. Berger et al., J. Pharmacol. Exp. Ther. 256, 883–889 (1991); Tidwell et al., supra (1990)). Final compounds were analyzed using high-performance liquid chromatography, proton nuclear magnetic resonance spectroscopy and elemental analysis.

Drugs. [$^3$H]idazoxan (specific activity 45 Ci/mmol) was purchased from Amersham (Arlington Heights, Ill., USA), cirazoline from Research Biochemicals International (Natick, Mass., USA), phenylmethyl sulfonyl fluoride from Boehringer Mannheim (Indianapolis, Ind., USA), sucrose from Fisher (Fair Lawn, N.J., USA) and Tris/HCl from Schwartz/Mann Biotech (Cleveland, Ohio, USA). Benzamidine, yohimbine, phentolamine, epinephrine and bovine serum albumin were purchased from Sigma (St. Louis, Mo., USA). 1,4-Dioxane and 4-methoxybenzonitrile were purchased from Aldrich (Milwaukee, Wis., USA), and HCl gas and ammonia from Matheson (Secaucus, N.J., USA). All other compounds were synthesized in our laboratory. Buffers were prepared using deionized water from Dracor Water Systems (Kensington, Md., USA).

Data analysis. Binding analyses, statistics and graphics were performed using Prism 2.01 (Graphpad Software, Inc., San Diego, Calif., USA). Binding parameters for inhibitors are given as mean±S.D. except Compounds 4 and 8 which are expressed as mean±95% confidence intervals due to limited supply of compound. The calculated log of the octanol:water partition coefficient (ClogP) was calculated using MedChem Software 3.5 (Daylight Chemical Information Systems, New Orleans, La., USA).

2. Results

[$^3$H]Idazoxan saturation binding in rat liver membranes. Rat liver membranes, prepared according to the method of Zonnenschein et al. (supra) were reported to be rich in imidazoline $I_2$ sites while excluding $\alpha_2$-adrenoceptors. Saturation binding analyses reported a $B_{max}$ of 438±30 fmol/mg protein with non-specific binding representing 10–15% of total binding, which conforms with the results reported by Zonnenschein et al. (1990). [$^3$H]Idazoxan bound the rat liver membranes with a $K_d$=14±2 nM for saturable binding. To confirm that $\alpha_2$-adrenoceptors were absent from the preparation, displacement experiments were performed using yohimbine, a selective $\alpha_2$-adrenoceptor antagonist; epinephrine, a selective $\alpha_2$-adrenoceptor agonist; phentolamine, an $a_2$-adrenoceptor antagonist; and cirazoline, an $\alpha_2$-adrenoceptor antagonist as competitive inhibitors of [$^3$H]idazoxan binding. FIG. 1 shows that selective $\alpha_2$-adrenoceptor ligands did not compete for radioligand binding, whereas phentolamine displaced [$^3$H] idazoxan binding with low affinity ($K_i$>5000), and cirazoline with high affinity ($K_i$=3.0±0.4 nM).

Competition binding studies. A competitive inhibition curve using pentamidine as the inhibitor of [$^3$H]idazoxan binding was generated (data not shown). The $K_i$ of 1.4±0.22 nM demonstrates that pentamidine binds to imidazoline $I_2$ sites with very high affinity, comparable to that of the most potent ligands. Several interesting structure/activity relationships were observed from the data in Table 1. Taking pentamidine (Compound 1) as the lead compound, no change in affinity was observed when the central alkyl link was increased to six carbons (Compound 2) or the amidine groups replaced with imidazoline moieties (Compound 3). Moderate reductions in affinity (10–100 nM) were observed when the alkyl chain was shortened further (Compounds 4 and 7) and a similar reduction was noted when one of the cations was replaced by a nitro group (Compound 8). Loss of one benzamidine moiety (Compound 9) caused a further reduction in affinity; however, when both the amidine phenoxy moiety and four of the carbons from the alkyl chain were removed from pentamidine (Compound 10), there was no further reduction in affinity when compared to Compound 9.

Interestingly, methoxy substitution meta to the cation (Compounds 5 and 6) produced varied results depending on the nature of the cationic moiety. When compared to the unsubstituted analog (Compound 7), methoxy substitution (Compound 6) resulted in over a two log decrease in imidazoline receptor binding. However, methoxy substitution of the imidazoline analog (Compound 5) resulted in a compound with similar affinity to Compound 7. The low affinity of Compound 6 may be a result of its very low ClogP. Likewise, a comparison of Compounds 10–12 shows that Compound 11 with the lowest ClogP of all the compounds evaluated also had the lowest affinity. The low affinity of Compound 11 may be due to the existence of contributing resonance structures to form a zwitterion. The basicity and therefore the binding property of the amidines are greatly influenced by the presence of different substituents on the benzamidine ring. Both benzamidine (Compound 12) and 4-methoxybenzamidine (Compound 10) display resonance stabilization of the positive charge throughout the molecule; however, the phenoxide ion of 4-hydroxybenzamidine neutralizes the positive charge, therefore making it unavailable for receptor binding. This molecule lends support to the theory that a strong cation is an important factor in receptor binding.

ClogP. ClogP increases as compound lipophilicity increases. Table 1 shows that Compound 3 is the most lipophilic (ClogP 6.0) and Compound 11 is the least lipophilic (ClogP=0.08) of the compounds tested. There is no significant correlation for the group as a whole between $K_i$ and ClogP; Pearson correlation coefficient r=−0.38 P=0.22. However, it is interesting to note that the ClogP and $K_i$ values for Compounds 5 and 6 differ considerably. The low affinity of Compound 6 ($K_i$≅3500 nM) may be attributed to its hydrophilic nature, denoted by the very low ClogP (0.09). Similarly, when Compounds 10–12 are compared, the derivative with the lowest ClogP (Compound 11) shows weakest affinity for the imidazoline $I_2$ site ($K_i$≅30,000 nM, ClogP=0.08).

TABLE 1

Affinity for $I_2$ binding sites, anti-*P. carinii* activity and ClogP values for pentamidine (Compound 1) and various analogs.

| | Structure | $K_i$(nM) | Hill Slope | ClogP |
|---|---|---|---|---|
| 1 | HN=C(NH$_2$)–C$_6$H$_4$–O–(CH$_2$)$_5$–O–C$_6$H$_4$–C(NH$_2$)=NH | 1.4 ± 0.22 | −0.8 | 2.3 |
| 2 | HN=C(NH$_2$)–C$_6$H$_4$–O–(CH$_2$)$_6$–O–C$_6$H$_4$–C(NH$_2$)=NH | 3.2 ± 0.36 | −1.2 | 2.8 |
| 3 | imidazoline–C$_6$H$_4$–O–(CH$_2$)$_5$–O–C$_6$H$_4$–imidazoline | 4.3 ± 1.09 | −0.8 | 6.0 |
| 4 | HN=C(NH$_2$)–C$_6$H$_4$–O–(CH$_2$)$_4$–O–C$_6$H$_4$–C(NH$_2$)=NH | 23.4 ± 6.8 | −0.8 | 1.8 |

TABLE 1-continued

Affinity for $I_2$ binding sites, anti-*P. carinii* activity and ClogP values for pentamidine (Compound 1) and various analogs.

| | Structure | $K_i$(nM) | Hill Slope | ClogP |
|---|---|---|---|---|
| 5 | imidazoline—Ph(OCH₃)—O—(CH₂)₃—O—Ph(OCH₃)—imidazoline | 50.1 ± 1.06 | −0.9 | 4.0 |
| 6 | H₂N(HN=)C—Ph(OCH₃)—O—(CH₂)₃—O—Ph(OCH₃)—C(=NH)NH₂ | ~3500 | −0.9 | .09 |
| 7 | H₂N(HN=)C—Ph—O—(CH₂)₃—O—Ph—C(=NH)NH₂ | 27.2 ± 7.63 | −0.8 | 1.3 |
| 8 | H₂N(HN=)C—Ph—O—(CH₂)₅—O—Ph—NO₂ | 62.0 ± 25 | −0.8 | 3.7 |
| 9 | H₂N(HN=)C—Ph—O—(CH₂)₅—OH | 319 ± 39.5 | −0.8 | .8 |
| 10 | H₂N(HN=)C—Ph—OCH₃ | 228 ± 36.5 | −0.8 | 0.7 |
| 11 | H₂N(HN=)C—Ph—OH | ~30,000 | −0.3 | .08 |
| 12 | H₂N(HN=)C—Ph | 580 ± 61.3 | −0.8 | 0.6 |

[a]Mean Histologic Score (compared to saline control; mean histologic score saline = 3.8 out of a possible 4.0). ND = not done. Binding in the presence of 5 nM [³H]idazoxan ($K_d$ 14 ± 2 nM). $B_{max}$ = 438 ± 30 fmol/mg protein. $K_i$ values are the result of at least three experiments expressed as mean Ki ± SD except compounds 4 and 8, which were derived from two experiments due to limited quantities of compound. These results are stated as mean Ki ± 95% confidence intervals.

Anti-Pneumocystis carinii activity. Pentamidine exhibits anti-*P. carinii* activity with a mean histologic score of 1.3. This is a moderately effective antimicrobial agent, having activity against a variety of organisms (B. Blagbum et al., Antimicrob. Agents Chemother. 35, 1520–1523 (1991); C. Bell et al., Antimicrob. Agents Chemother. 35, 1099–1107 (1991); D. Lindsay et al., Antimicrob. Agents Chemother. 35, 1914–1916 (1991)). Five of the compounds have anti-*P. carinii* activity greater than pentamidine (Compounds 2,3, 4,5,6), while 2 of the compounds have no activity at all (Compounds 9,11). Compounds 5 and 6 are equally effective anti-*P.carinii* agents, yet their respective affinities for the imidazoline 12 site differ 70-fold. These compounds provide an example that affinity for the imidazoline $I_2$ site does not correlate to anti-*P. carinii* activity; Pearson correlation coefficient r=0.60 P=0.09.

EXAMPLE 2 AND 3

The compounds set forth in Table 2 and Table 3 below, which are either known and can be synthesized in accordance with known techniques as described above or variations thereof which will be apparent to those skilled in the art, are also illustrative of the present invention.

TABLE 2

IMIDAZOLNE RECEPTOR BINDING COMPOUNDS

| Compound | Structure | Ki(nM) |
|---|---|---|
| 001 KAO 011 | 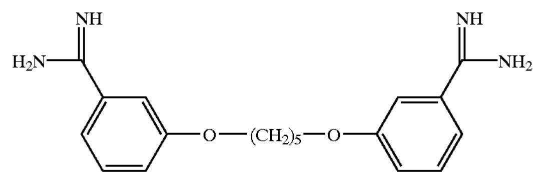 | 158.0 |
| BABIM | 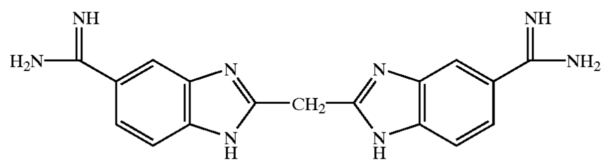 | 7,512 |
| BABB | 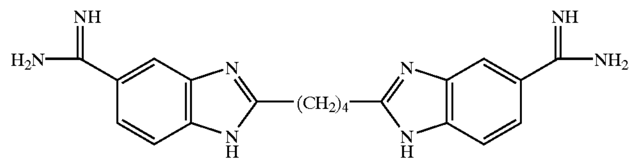 | 5,526 |
| BIBB | 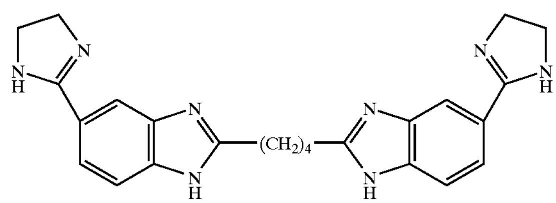 | 44,780 |
| DB 205 | 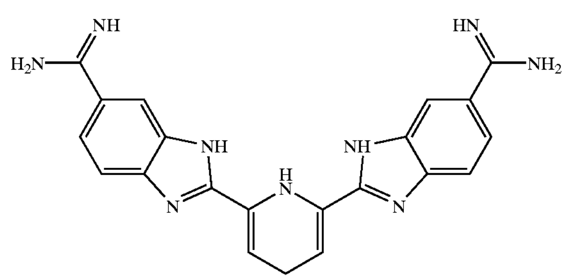 | 346,700 |
| DB 183 | 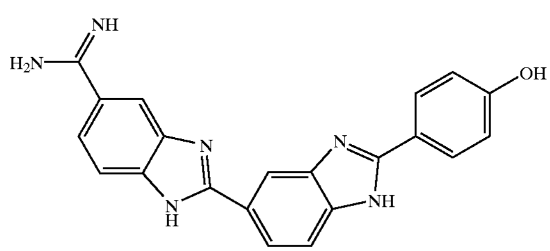 | 65,640 |
| 003 KAO 111 | 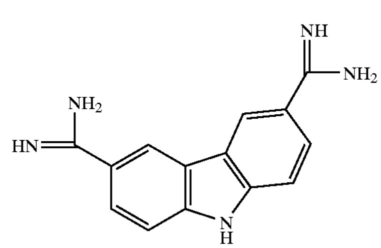 | 44,700 |

TABLE 2-continued

IMIDAZOLNE RECEPTOR BINDING COMPOUNDS

| Compound | Structure | Ki(nM) |
|---|---|---|
| DAP 092 | (carbazole-2,7-bis(carboxamidine)) | 18,090 |
| DB 75 | 2,5-bis(4-amidinophenyl)furan | 653 |
| DB 60 | 2,5-bis[4-(2-imidazolinyl)phenyl]furan | 630 |
| DB 181 | 2,5-bis[4-(N-isopropylamidino)phenyl]furan | 5,503 |
| DB 244 | 2,5-bis[4-(N-cyclopentylamidino)phenyl]furan | 6,755 |
| DB 103 | 2,5-bis[4-(1,4,5,6-tetrahydropyrimidin-2-yl)phenyl]furan | 236.0 |
| DB 351 | 2,5-bis(4-amidinophenyl)thiophene | 110.6 |
| DB 262 | 2,5-bis(4-amidinophenyl)pyrrole | 3,785 |

TABLE 3

IMIDAZOLINE RECEPTOR BINDING COMPOUNDS

| Compound | Structure | Ki(nM) |
|---|---|---|
| MC 96 | H$_2$N-C(=NH)-C$_6$H$_4$-CH$_2$O-C$_6$H$_4$-C(=NH)-NH$_2$ | 1.4 |
| FS 44 | H$_2$N-C(=NH)-C$_6$H$_4$-CH$_2$O-C$_6$H$_5$ | 2.8 |
| FS 104 | C$_6$H$_5$-CH$_2$O-C$_6$H$_4$-C(=NH)-NH$_2$ | 1.5 |
| FS 113 | H$_2$N-C(=NH)-C$_6$H$_4$-CH$_2$O-C$_6$H$_4$-OCH$_3$ | 2.2 |
| MC97c | H$_2$N-C(=NH)-C$_6$H$_4$-CH$_2$O-C$_6$H$_4$-C(=NH)-NH$_2$ (meta) | 1215 |
| FS 117 | C$_6$H$_5$-CH$_2$O-C$_6$H$_4$-C(=NH)-NH$_2$ (meta) | 32.7 |

The foregoing is illustrative of the present invention, and is not to be construed as limiting thereof. The invention is defined by the following claims, with equivalents of the claims to be included therein.

We claim:

1. A method of binding the imidazoline receptor, comprising: contacting a bis-benzene to said imidazoline receptor in an amount effective to bind to said receptor, wherein said bis-benzene contains at least one amidine group, wherein said contacting step is carried out in vivo by administering said compound to a subject afflicted with a disease state which is alleviable by treatment with a compound having high selectivity and affinity for the imidazoline receptor site.

2. A method according to claim 1, wherein said bis-benzene has the formula I:

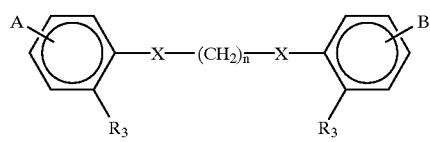

wherein:

A and B are each independently selected from the group consisting of H, loweralkyl, oxyalkyl, nitro, amino, aminoalkyl, halo, hydroxy, carboxy, and compounds of formula (i):

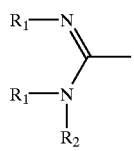

subject to the proviso that at least one of A and B is a compound of formula (i);

R$_1$ and R$_2$ are each independently selected from the group consisting of H, loweralkyl, oxyalkyl, alkoxyalkyl, cycloalkyl, aryl, hydroxyalkyl, aminoalkyl and alkylaminoalkyl; or two R$_1$ groups on the same amidine group together represent —(CH$_2$)$_m$— wherein m is 2, 3, or 4;

R$_3$ is H, loweralkyl, oxyalkyl, alkoxyalkyl, hydroxyalkyl, cycloalkyl, aryl, aminoalkyl, alkylaminoalkyl or halogen;

n is from 2 to 6; and

X is O, NH, or S;

or a pharmaceutically acceptable salt thereof.

3. A method according to claim 2, wherein R$_1$, R$_2$ and R$_3$ are H; wherein X is O; and wherein n is 5.

4. A method according to claim 1, wherein said bis-benzene has the formula II:

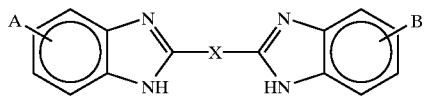

wherein:

A and B are each independently selected from the group consisting of H, loweralkyl, oxyalkyl, nitro, amino, aminoalkyl, halo, hydroxy, carboxy, and compounds of formula (i):

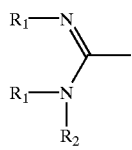

subject to the proviso that at least one of A and B is a compound of formula (i);

$R_1$ and $R_2$ are each independently selected from the group consisting of H, loweralkyl, oxyalkyl, alkoxyalkyl, cycloalkyl, aryl, hydroxyalkyl, aminoalkyl and alkylaminoalkyl; or two $R_1$ groups on the same amidine group together represent —(CH$_2$)m— wherein m is 2, 3, or 4;

$R_3$ is H, loweralkyl, oxyalkyl, alkoxyalkyl, hydroxyalkyl, cycloalkyl, aryl, aminoalkyl, alkylaminoalkyl or halogen;

X is linear or branched, saturated or unsaturated C1–C12 alkyl containing up to 4 double bonds; or X is a heterocyclic aromatic group selected from the group consisting of:

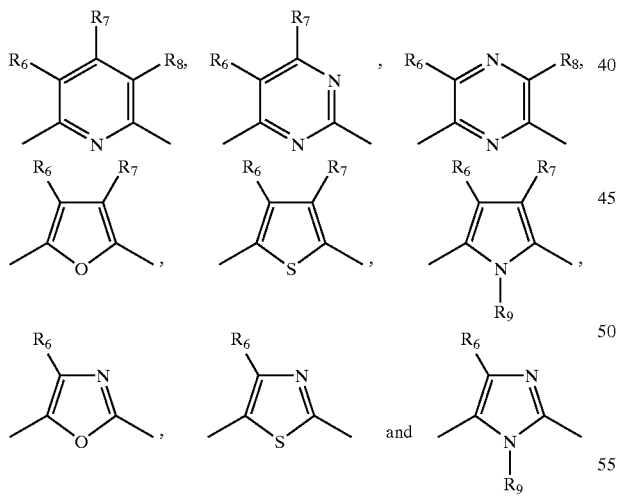

wherein
$R_6$, $R_7$, and $R_8$ are each independently selected from the group consisting of H, loweralkyl, halogen, oxyalkyl, oxyaryl, or oxyarylalkyl;
$R_9$ is hydrogen, loweralky, hydroxy, aminoalkyl or alkylaminoalkyl;
or the pharmaceutically acceptable salts thereof.

5. A method according to claim 1, wherein said bisbenzene has the formula III:

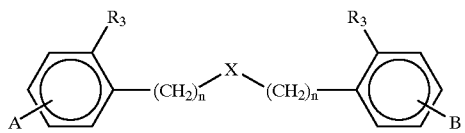

wherein:

A and B are each independently selected from the group consisting of H, loweralkyl, oxyalkyl, nitro, amino, aminoalkyl, halo, hydroxy, carboxy, and compounds of formula (i):

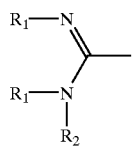

subject to the proviso that at least one of A and B is a compound of formula (i);

$R_1$ and $R_2$ are each independently selected from the group consisting of H, loweralkyl, oxyalkyl, alkoxyalkyl, cycloalkyl, aryl, hydroxyalkyl, aminoalkyl and alkylaminoalkyl; or two $R_1$ groups on the same amidine group together represent —(CH$_2$)m—wherein m is 2, 3, or 4;

$R_3$ is H, loweralkyl, oxyalkyl, alkoxyalkyl, hydroxyalkyl, cycloalkyl, aryl, aminoalkyl, alkylaminoalkyl or halogen;

or two $R_1$ groups on the same amidine group together represent

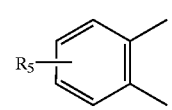

wherein $R_5$ is

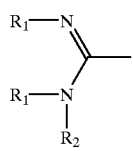

n is an integer from 0 to 2; and
X is CH$_2$O or is a heterocyclic aromatic group selected from the group consisting of:

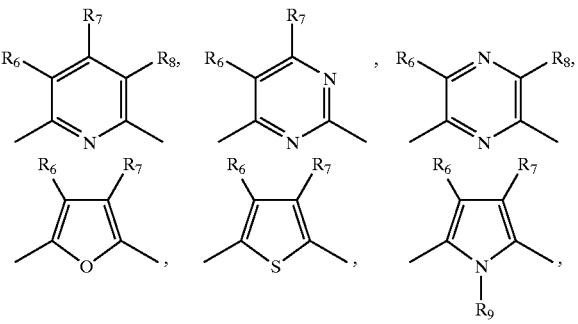

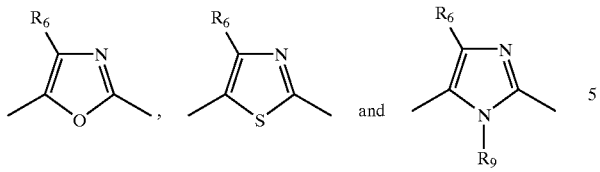

wherein

R$_6$, R$_7$, and R$_8$ are each independently selected from the group consisting of H, loweralkyl; halogen, oxyalkyl, oxyaryl, or oxyarylalkyl;

R$_9$ is hydrogen, loweralkyl, hydroxy, aminoalkyl or alkylaminoalkyl;

and the pharmaceutically acceptable salts thereof.

6. A method according to claim 1, wherein said bis-benzamidine has the formula IV:

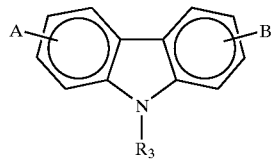

A and B are each independently selected from the group consisting of H, loweralkyl, oxyalkyl, nitro, amino, aminoalkyl, halo, hydroxy, carboxy, and compounds of formula (i):

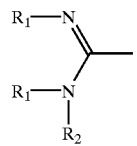

subject to the proviso that at least one of A and B is a compound of formula (i);

R$_1$ and R$_2$ are each independently selected from the group consisting of H, loweralkyl, oxyalkyl, alkoxyalkyl, cycloalkyl, aryl, hydroxyalkyl, aminoalkyl and alkylaminoalkyl; or two R$_1$ groups on the same amidine group together represent —(CH$_2$)$_m$— wherein m is 2, 3, or 4;

R$_3$ is H, loweralkyl, oxyalkyl, alkoxyalkyl, hydroxyalkyl, cycloalkyl, aryl, aminoalkyl, alkylaminoalkyl or halogen;

or two R$_1$ groups on the same amidine group together represent

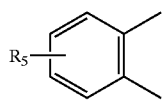

wherein R$_5$ is

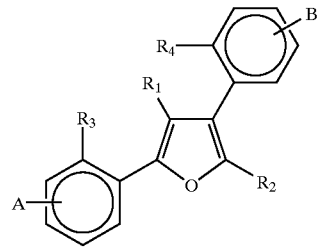

and the pharmaceutically acceptable salts thereof.

7. A method according to claim wherein said bis-benzamidine has the formula (V):

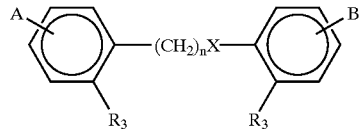

wherein:

A and B are each independently selected from the group consisting of H, loweralkyl, oxyalkyl, nitro, amino, aminoalkyl, halo, hydroxy, carboxy, and compounds of formula (ii):

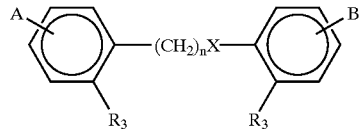

subject to the proviso that at least one of A and B is a substituent of formula (ii);

R$_1$ and R$_2$ are each independently selected from the group consisting of H, loweralkyl, aryl, alkylaryl, aminoaryl, halogen, oxyalkyl, oxyaryl, or oxyarylalkyl;

R$_3$ and R$_4$ are each independently selected from the group consisting of H, loweralkyl, oxyalkyl, alkylaryl, aryl, oxyaryl, aminoalkyl, aminoaryl, or halogen; and each R$_5$ is independently selected from the group consisting of H, loweralkyl, alkoxyalkyl, hydroxyalkyl, aminoalkyl, alkylaminoalkyl, cycloalkyl, aryl, or alkylaryl or two R$_5$ groups together represent C$_2$ to C$_{10}$ alkyl, hydroxyalkyl, or alkylene; and R$_6$ is H, hydroxy, loweralky, alkoxyalkyl, hydroxyalkyl, aminoalkyl, alkylamino, alkylaminoalkyl, cycloalkyl, hydroxycycloalkyl, alkoxycycloalkyl, aryl, or alkylaryl;

or a pharmaceutically acceptable salt thereof.

8. A method according to claim 1, wherein said bis-benzene has the formula VI:

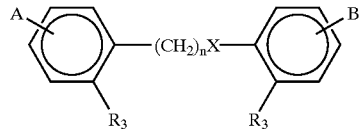

wherein:

A and B are each independently selected from the group consisting of H, loweralkyl, oxyalkyl, nitro, amino, aminoalkyl, halo, hydroxy, carboxy, and compounds of formula (i):

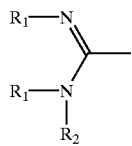

subject to the proviso that at least one of A and B is a substituent of formula (i);

$R_1$ and $R_2$ are each independently selected from the group consisting of H, loweralkyl, oxyalkyl, alkoxyalkyl, cycloalkyl, aryl, hydroxyalkyl, aminoalkyl and alkylaminoalkyl; or two R, groups on the same amidine group together represent —($CH_2$)m—wherein m is 2, 3, or 4;

$R_3$ is H, loweralkyl, oxyalkyl, alkoxyalkyl, hydroxyalkyl, cycloalkyl, aryl, aminoalkyl, alkylaminoalkyl or halogen;

or two $R_1$ groups on the same amidine group together represent

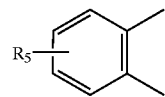

wherein $R_5$ is

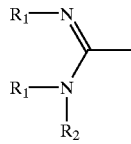

X is O, S, or NH;

n is an integer from 1 to 8;

and the pharmaceutically acceptable salts thereof.

* * * * *